US010299753B2

(12) United States Patent
Govari et al.

(10) Patent No.: US 10,299,753 B2
(45) Date of Patent: May 28, 2019

(54) FLASHLIGHT VIEW OF AN ANATOMICAL STRUCTURE

(75) Inventors: Assaf Govari, Haifa (IL); Andres Claudio Altmann, Haifa (IL); Yitzhack Schwartz, Haifa (IL)

(73) Assignee: BIOSENSE WEBSTER, INC., Diamond Bar, CA (US)

( * ) Notice: Subject to any disclaimer, the term of this patent is extended or adjusted under 35 U.S.C. 154(b) by 867 days.

(21) Appl. No.: 11/946,983

(22) Filed: Nov. 29, 2007

(65) Prior Publication Data
US 2009/0143677 A1 Jun. 4, 2009

(51) Int. Cl.
| | |
|---|---|
| *A61B 5/00* | (2006.01) |
| *A61B 5/06* | (2006.01) |
| *A61B 6/00* | (2006.01) |
| *A61B 8/00* | (2006.01) |
| *A61B 8/08* | (2006.01) |

(Continued)

(52) U.S. Cl.
CPC ............ *A61B 6/5247* (2013.01); *A61B 5/062* (2013.01); *A61B 8/0883* (2013.01); *A61B 8/12* (2013.01); *A61B 8/4254* (2013.01); *A61B 8/5238* (2013.01); *A61B 8/543* (2013.01); *A61B 5/7285* (2013.01); *A61B 6/503* (2013.01);
(Continued)

(58) Field of Classification Search
CPC ........ H04N 5/262; H04N 5/2628; A61B 8/14; A61B 8/483; A61B 8/461; A61B 6/5247; A61B 6/00; A61B 5/062; A61B 5/06; A61B 8/4254; A61B 8/00; A61B 8/12; A61B 8/5238; A61B 8/08; A61B 8/543; A61B 8/0883; A61B 2090/364; A61B 90/00; A61B 2034/2051; A61B 34/20; A61B 8/445; A61B 5/7285; A61B 5/00; A61B 6/541; A61B 6/503; G01S 7/52085; G01S 15/8993; G01S 7/52074; G03B 42/06; G06T 3/4092
USPC .......................................... 600/426, 462, 424
See application file for complete search history.

(56) References Cited

U.S. PATENT DOCUMENTS

| | | | |
|---|---|---|---|
| 5,738,096 | A | 4/1998 | Ben-Haim |
| 6,019,725 | A | 2/2000 | Vesely et al. |

(Continued)

FOREIGN PATENT DOCUMENTS

| | | |
|---|---|---|
| CN | 1853574 A | 11/2006 |
| CN | 101035468 A | 9/2007 |

(Continued)

OTHER PUBLICATIONS

EP Search Report EP 08 25 3843 Dated Jan. 5, 2012.
(Continued)

*Primary Examiner* — Thomas J Hong
*Assistant Examiner* — Helene Bor
(74) *Attorney, Agent, or Firm* — Notaro, Michalos & Zaccaria P.C.

(57) ABSTRACT

A method for imaging an anatomical structure on a display, including acquiring an initial spatial representation of the anatomical structure and positioning an instrument in proximity to the anatomical structure. The method further includes determining a location of the instrument, and generating, in response to the location, an image of a part of the anatomical structure. The method includes appending the image to the initial spatial representation to display a combined spatial representation.

19 Claims, 5 Drawing Sheets

(51) Int. Cl.
*A61B 8/12* (2006.01)
*A61B 34/20* (2016.01)
*A61B 90/00* (2016.01)

(52) U.S. Cl.
CPC ............... *A61B 6/541* (2013.01); *A61B 8/445* (2013.01); *A61B 2034/2051* (2016.02); *A61B 2090/364* (2016.02)

(56) References Cited

U.S. PATENT DOCUMENTS

| | | | |
|---|---|---|---|
| 6,049,622 | A | 4/2000 | Robb et al. |
| 6,203,497 | B1 | 3/2001 | Dekel et al. |
| 6,332,089 | B1 | 12/2001 | Acker et al. |
| 6,556,695 | B1 | 4/2003 | Packer et al. |
| 6,618,612 | B1 | 9/2003 | Acker et al. |
| 6,650,927 | B1 | 11/2003 | Keidar |
| 6,690,963 | B2 | 2/2004 | Ben-Haim et al. |
| 6,716,166 | B2 | 4/2004 | Govari |
| 6,773,402 | B2 | 8/2004 | Govari et al. |
| 6,778,846 | B1 * | 8/2004 | Martinez ............... A61B 90/36 600/407 |
| 6,892,090 | B2 | 5/2005 | Verard et al. |
| 6,990,368 | B2 * | 1/2006 | Simon et al. ................ 600/425 |
| 7,020,512 | B2 | 3/2006 | Ritter et al. |
| 7,263,397 | B2 * | 8/2007 | Hauck et al. ................ 600/374 |
| 2002/0049375 | A1 * | 4/2002 | Strommer et al. ............ 600/407 |
| 2003/0135112 | A1 | 7/2003 | Ritter et al. |
| 2003/0231789 | A1 | 12/2003 | Willis et al. |
| 2004/0068178 | A1 | 4/2004 | Govari |
| 2004/0147920 | A1 | 7/2004 | Keidar |
| 2005/0024507 | A1 * | 2/2005 | Katayama et al. ....... 348/231.99 |
| 2005/0203394 | A1 | 9/2005 | Hauck |
| 2005/0228280 | A1 | 10/2005 | Ustuner et al. |
| 2006/0182320 | A1 | 7/2006 | Peszynski et al. |
| 2006/0253032 | A1 * | 11/2006 | Altmann ............... A61B 5/042 600/466 |
| 2007/0027392 | A1 | 2/2007 | Schwartz |
| 2007/0038065 | A1 * | 2/2007 | Creighton, IV ....... A61B 5/062 600/407 |
| 2007/0167801 | A1 | 7/2007 | Webler et al. |

FOREIGN PATENT DOCUMENTS

| | | |
|---|---|---|
| DE | 10 2006 013476 B4 | 10/2007 |
| JP | 2000-135215 | 5/2000 |
| JP | 2002-119507 | 4/2002 |
| JP | 2005529701 A | 10/2005 |
| JP | 2006305357 A | 11/2006 |
| JP | 2006312037 A | 11/2006 |
| JP | 2007-296362 | 11/2007 |
| WO | WO 2003107251 A3 | 12/2003 |
| WO | WO 2006/038182 A1 | 4/2006 |
| WO | WO 2006038182 A1 | 4/2006 |

OTHER PUBLICATIONS

JP Patent Application 2008-303854 Office Action dated Feb. 4, 2014.
CN Patent Application 2008-10190810.2 Office Action dated Nov. 12, 2012.
CN Patent Application 2012-1022-729.0 Office Action dated Nov. 22, 2013.
U.S. Appl. No. 11/946,983 Dated Nov. 29, 2007—Pending.
CN Patent Application 2012-1022-729.0 Office Action dated Jul. 11, 20014.
CN Patent Application 2012-1022-729.0 Office Action dated Dec. 22, 2014.
JP Patent Application No. 2008-303854 Office Action dated Apr. 9, 2013.
AU Application 2008249201 Exam Report dated Feb. 28, 2013.
CA Application 2644886 Exam Report dated Apr. 21, 2015.
CA Application 2644886 Exam Report dated Jan. 6, 2016.
CN Application 201210220729.0 Office Action dated Dec. 2, 2013.
Canadian Search Report for Canada Application No. 2,644,886 filed Nov. 26, 2008.
First Examination Report for corresponding Indian application No. 2024/KOL/2008, dated Dec. 5, 2017.

* cited by examiner

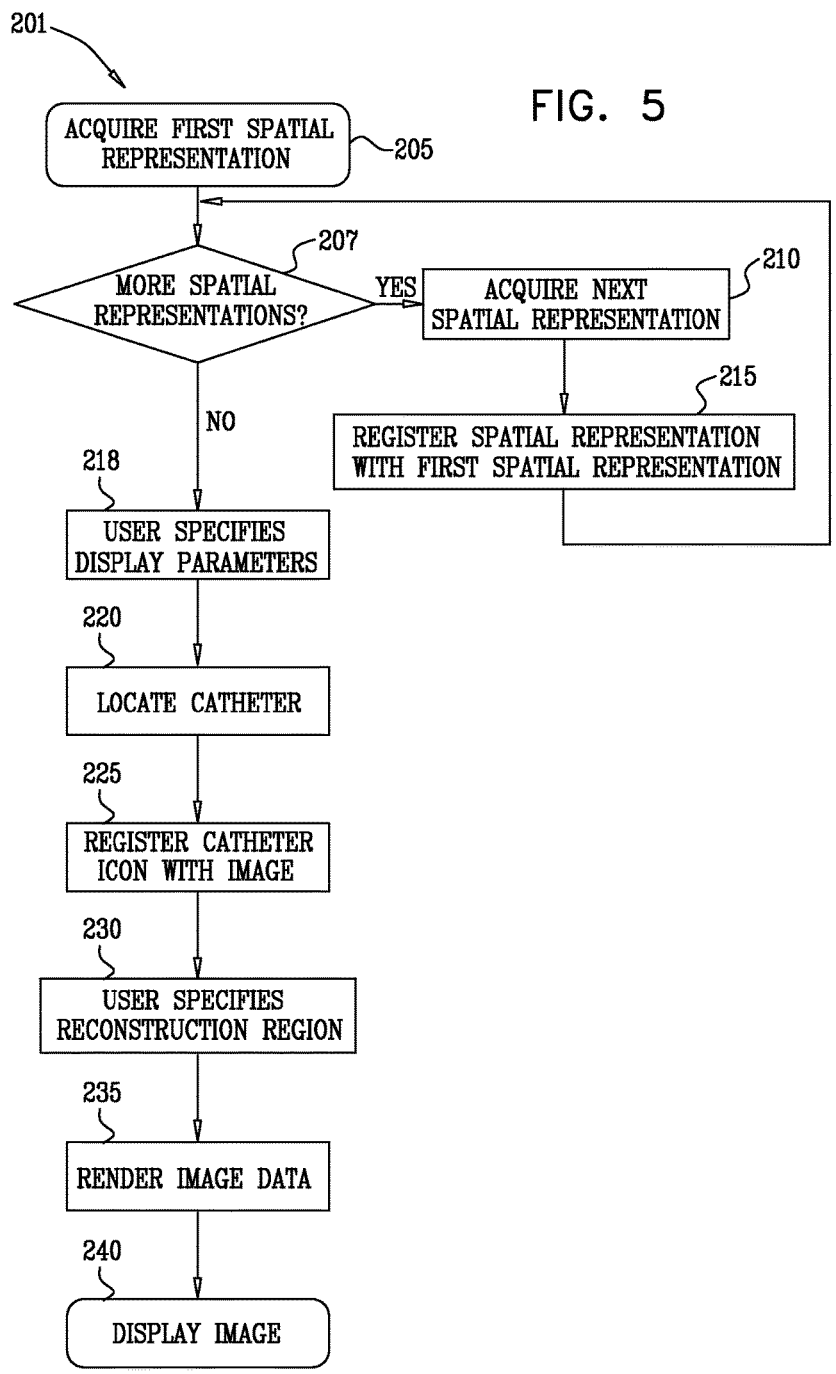

FLASHLIGHT VIEW OF AN ANATOMICAL STRUCTURE

FIELD OF THE INVENTION

The present invention relates generally to imaging, and in particular to medical imaging of an anatomical structure.

BACKGROUND OF THE INVENTION

Three-dimensional (3-D) ultrasound images of the heart are useful in many catheter-based diagnostic and therapeutic applications. Real-time imaging improves physician performance and enables even relatively inexperienced physicians to perform complex surgical procedures more easily. Three-dimensional imaging also reduces the time needed to perform some surgical procedures.

Methods for 3-D mapping of the endocardium (i.e., the inner surfaces of the heart) are known in the art. For example, U.S. Pat. No. 5,738,096 to Ben-Haim, which is assigned to the assignee of the present invention, and whose disclosure is incorporated herein by reference, describes a method for constructing a map of the heart. An invasive probe or catheter is brought into contact with multiple locations on the wall of the heart. The position of the invasive probe is determined for each location, and the positions are combined to form a structural map of at least a portion of the heart.

In some systems, such as the one described by U.S. Pat. No. 5,738,096 cited above, additional physiological properties, as well as local electrical activity on the surface of the heart, are also acquired by the catheter. A corresponding map incorporates the acquired local information.

Some systems use hybrid catheters that incorporate position sensing. For example, U.S. Pat. No. 6,690,963 to Ben-Haim et al., which is assigned to the assignee of the present invention, and whose disclosure is incorporated herein by reference, describes a locating system for determining the location and orientation of an invasive medical instrument.

A catheter with acoustic transducers may be used for non-contact imaging of the endocardium. For example, U.S. Pat. Nos. 6,716,166 to Govari, and 6,773,402 to Govari et al., which are assigned to the assignee of the present invention, and whose disclosures are also incorporated herein by reference, describe a system for 3-D mapping and geometrical reconstruction of body cavities, particularly of the heart. The system uses a cardiac catheter comprising a plurality of acoustic transducers. The transducers emit ultrasound waves that are reflected from the surface of the cavity and are received again by the transducers. The distance from each of the transducers to a point or area on the surface opposite the transducer is determined, and the distance measurements are combined to reconstruct the 3-D shape of the surface. The catheter also comprises position sensors, which are used to determine location and orientation coordinates of the catheter within the heart.

Typically, such systems provide an "endoscopic view", in which a reconstructed image is presented as it would appear if viewed through a certain catheter or other probe. For example, U.S. Pat. No. 6,556,695, to Packer et al., whose disclosure is incorporated herein by reference, describes a method for producing high resolution real-time images of a heart. During a medical procedure such as endocardial physiology mapping and ablation, real-time images are produced by an ultrasonic transducer inserted into the heart. A high resolution heart model is registered with the acquired real-time images and is used to produce dynamic, high resolution images for display during the procedure. Different parts of the anatomy may be viewed by moving a catheter distal end to "aim" an acoustic transducer at structures of interest. A joystick may be used to scan away from the field of view of the ultrasonic transducer when other parts of the anatomy are to be examined without moving the catheter. An orientation within the anatomic structure (e.g. heart chamber) is maintained using navigation icons as described in U.S. Pat. No. 6,049,622, to Robb et al., whose disclosure is also incorporated herein by reference.

Similarly, U.S. Pat. No. 6,203,497, to Dekel et al., whose disclosure is also incorporated herein by reference, describes a system and method for visualizing internal images of an anatomical body. Internal images of the body are acquired by an ultrasonic imaging transducer, which is tracked in a frame of reference by a spatial determinator. The position of the images in the frame of reference is determined by calibrating the ultrasonic imaging transducer to produce a vector position of the images with respect to a fixed point on the transducer. This vector position can then be added to the location and orientation of the fixed point of the transducer in the frame of reference determined by the spatial determinator. The location and orientation of a medical instrument used on the patient are also tracked in the frame of reference by spatial determinators. This information is used to generate processed images from a view spatially related to the location of the instrument.

U.S. Pat. No. 6,892,090, to Verard et al, whose disclosure is incorporated herein by reference, describes a method and apparatus for virtual endoscopy. A surgical instrument navigation system is provided that visually simulates a virtual volumetric scene of a body cavity of a patient from a point of view of a surgical instrument residing in the cavity of the patient.

Some systems display the ultrasonic catheter tip together with the ultrasound images, as a navigation and imaging guide. For example, U.S. Pat. No. 6,019,725, to Vesely et al., whose disclosure is also incorporated herein by reference, describes a 3-D tracking and imaging system for tracking the position of a surgical instrument (e.g., a catheter, probe, a sensor, needle or the like) inserted into a body, and displaying a 3-D image showing the position of the surgical instrument in reference to a 3-D image of the environment surrounding the surgical instrument. The 3-D tracking and imaging system aids a physician in the guidance of the surgical instrument inside the body.

U.S. Pat. No. 7,020,512, to Ritter et al., whose disclosure is incorporated herein by reference, describes a method of localizing a medical device inside a patient's body. AC magnetic signals of different frequencies are transmitted between points of known location outside of the patient's body and points on the medical device inside the patient's body. The transmitted AC magnetic signals are then processed to determine the position of the points on the medical device, and thus the location of the medical device. This processing includes correcting for the effects of metal in the vicinity by using the transmitted and received signals at different frequencies.

U.S. Pat. No. 7,020,512 also describes an alternative embodiment, in which a reference device is provided inside the patients' body, and the medical device is localized relative to the reference catheter. The use of signals comprising at least two frequencies may or may not be used in this relative localization embodiment, but typically are used at least to localize the reference catheter.

SUMMARY OF THE INVENTION

A three or four dimensional (3-D or 4-D, collectively also written herein as n-D) ultrasound image of an anatomical structure, such as the heart, contains a huge amount of visual information—so much information that it is often difficult for a viewer to understand and distinguish features of interest from the surrounding background. The present invention addresses this problem by permitting the viewer, typically a system operator or a physician, hereinbelow referred to as an operator, to select and view only a small part of an overall n-D image. The part is referred to herein as a "reconstruction region," and is typically user-selected to be within a certain distance of an instrument which is in proximity to, and in some embodiments within, the anatomical structure. Typically, the anatomical structure is an organ and the instrument is a catheter inserted into the organ.

In one embodiment, the reconstruction region is appended to a 3-D spatial representation, typically a map, of the organ, into which an actual instrument has typically been inserted. The n-D ultrasound image may be displayed only within the limited reconstruction region described above. Alternatively, outside the region, the n-D ultrasound image may be displayed differently from its display within the region. The difference may be in color, transparency/opacity, resolution, or other image display parameters, or a combination of these parameters, the difference typically being chosen to enhance the visibility of elements within the region. In addition, outside the region the operator may choose to display, or not to display, the 3-D spatial representation.

In an alternative embodiment, the reconstruction region is not appended to a 3-D spatial representation. Rather, the operator displays only the n-D ultrasound image within the reconstruction region. Alternatively, the operator may display the n-D ultrasound image in one form within the reconstruction region, and in another different form outside the region, using different image display parameters substantially as described above.

The operator is thus presented with a display of anatomical features in the vicinity of a location of interest, for example, where a catheter tip is positioned or where an ultrasound catheter is aimed. From the display the operator may visualize where the actual instrument is in relation to the portion of the part of the organ being imaged. The display thus allows the operator to maintain a visual understanding of local features within the organ. The display is referred to hereinbelow as a flashlight view.

In some embodiments an icon representing the instrument may be presented on the flashlight view, in registration with the reconstruction region.

The reconstruction region may typically be defined by one or more of the following methods, selectable by the operator:

Relative to a location of an inserted instrument, for example, the tip of a catheter.
Relative to a direction of an ultrasound beam from an instrument such as an ultrasound generator. The region in this case is typically a volumetric slice, having a given thickness, in the direction of the beam.
The operator may change the size and location of the region, typically by using a pointing device such as a mouse.

For the first two methods, the operator may configure the display to update as the instrument moves, or the display may be "frozen" at a selected location.

There is therefore provided, according to an embodiment of the present invention, a method for imaging an anatomical structure on a display, including:

acquiring an initial spatial representation of the anatomical structure;

positioning an instrument in proximity to the anatomical structure;

determining a location of the instrument;

generating, in response to the location, an image of a part of the anatomical structure;

appending the image to the initial spatial representation to display a combined spatial representation.

Typically the instrument includes a catheter configured to generate an ultrasound beam, and generating the image includes generating the image in response to a direction of the ultrasound beam. Generating the image may include using a pointing device to delineate extents of the part of the anatomical structure.

In an embodiment displaying the combined spatial representation includes displaying the image using image display parameters and displaying the initial spatial representation using spatial representation display parameters different from the image display parameters. The image display parameters and the spatial representation display parameters may be chosen from parameters including intensity, color, resolution, and transparency.

In one embodiment the method includes generating a definition of the image of the part of the anatomical structure that delineates extents of the image, and applying the definition to the initial spatial representation to form a redefined spatial representation, and appending the image includes appending the image to the redefined spatial representation.

The anatomical structure may include a surface of an anatomical organ.

The method may include superimposing an icon representing the instrument in registration with the combined spatial representation.

Typically, the initial spatial representation includes at least one of a Carto map, a Computed Tomographic (CT) image, and a magnetic resonance (MR) image.

Alternatively, the initial spatial representation includes an ultrasound image, and the image of the part of the anatomical structure includes a section of the ultrasound image. The section may include a fraction of the ultrasound image, the fraction being in a range between 10% and 50%.

Typically, positioning the instrument includes positioning the instrument within the anatomical structure.

In a disclosed embodiment, the method includes determining an orientation of the instrument, and generating the image includes generating the image in response to the orientation.

There is further provided, according to an embodiment of the present invention, a computer software product for imaging an anatomical structure on a display, including a tangible computer-readable medium in which computer instructions are stored, which instructions, when read by a computer, cause the computer to acquire an initial spatial representation of the anatomical structure, to determine a location of an instrument which is in proximity to the anatomical structure, to generate, in response to the location, an image of a part of the anatomical structure, to append the image to the initial spatial representation so as to form a combined spatial representation, and to display the combined spatial representation.

There is further provided, according to an embodiment of the present invention a method for imaging an anatomical structure on a display, including:

positioning an instrument in proximity to the anatomical structure;

determining a location of the instrument;

generating, in response to the location, an image of the anatomical structure;

defining a partial region of the image in response to the location;

applying first display parameters to the image within the partial region and second display parameters, different from the first display parameters, to the image outside the partial region, so as to form a composite image; and presenting the composite image on the display.

In an embodiment applying the second display parameters includes displaying the image outside the partial region with no image information therein.

Typically the instrument includes a catheter configured to generate an ultrasound beam, and defining the partial region includes delineating extents of the region in response to a direction of the beam.

There is further provided, according to an embodiment of the present invention, apparatus for imaging an anatomical structure, including:

an instrument which is configured to be positioned in proximity to the anatomical structure; and a processor, which is configured to be coupled to the instrument, and which is arranged to acquire an initial spatial representation of the anatomical structure, to determine a location of the instrument, to generate, in response to the location, an image of a part of the anatomical structure, and to append the image on the initial spatial representation, so as to present a combined spatial representation on a display.

There is further provided, according to an embodiment of the present invention, apparatus for imaging an anatomical structure on a display, including:

an instrument which is configured to be positioned in proximity to the anatomical structure; and a processor which is configured to determine a location of the instrument, to generate, in response to the location, an image of the anatomical structure, to define a partial region of the image in response to the location, to apply first display parameters to the image within the partial region and second display parameters, different from the first display parameters, to the image outside the partial region, so as to form a composite image, and present the composite image on the display.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein:

FIG. 5 is a flowchart illustrating a method of displaying the flashlight views illustrated in FIGS. 3, 4A, and 4B, in accordance with a disclosed embodiment of the present invention.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a tangible computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

Embodiments of the present invention may be used for viewing images of different anatomical structures, typically structures comprising cavities. Hereinbelow, by way of example, the anatomical structure is assumed to comprise the heart of a patient.

Figure 1:
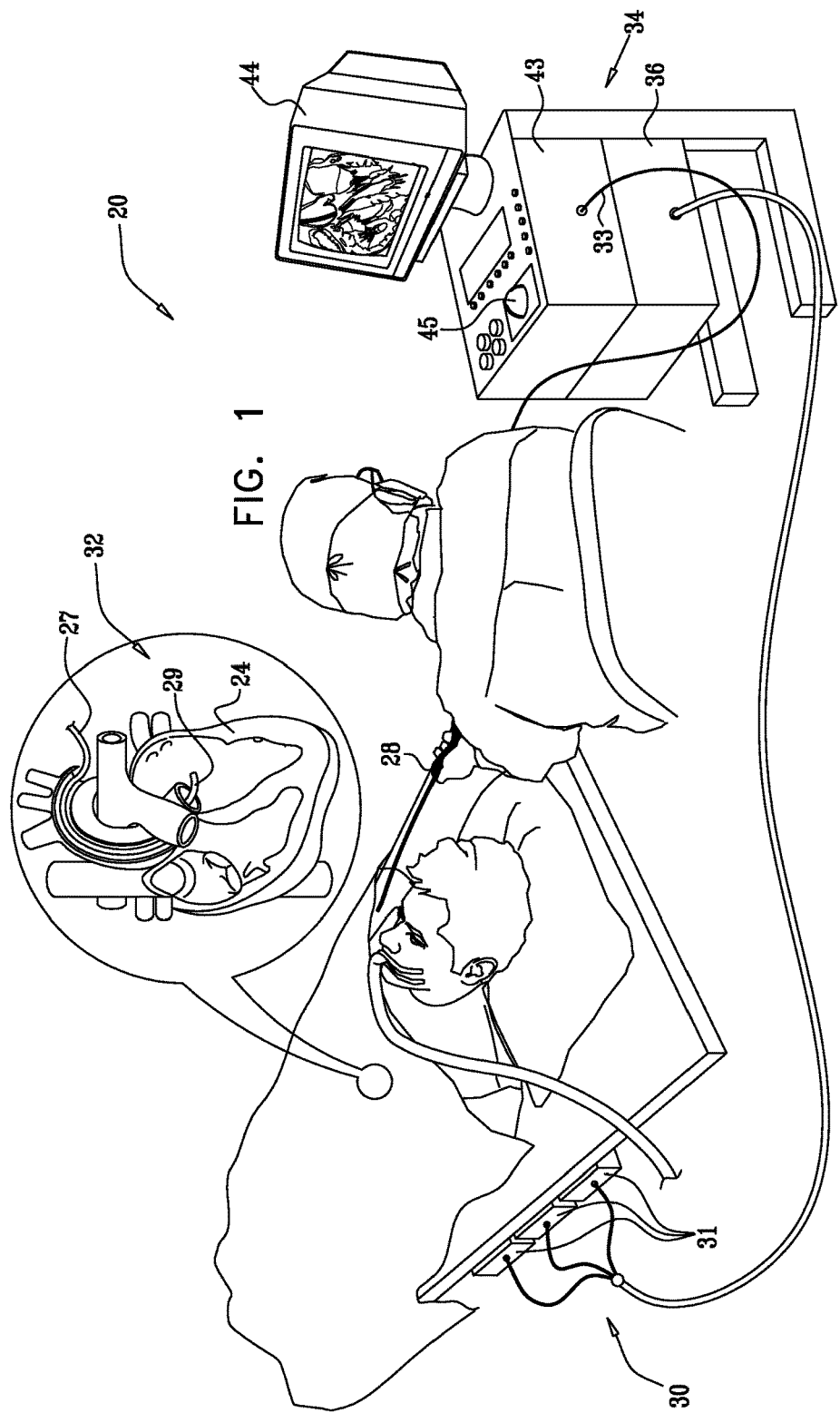
FIG. 1 is a pictorial illustration of a system for acquiring a flashlight view of a heart, in accordance with a disclosed embodiment of the present invention.

Turning now to the drawings, reference is initially made to FIG. 1, which is a pictorial illustration of a system 20 for acquiring a flashlight view of a heart 24, in accordance with a disclosed embodiment of the invention. System 20 comprises a catheter 27, which is inserted by an operator of system 20, herein assumed to be a physician, into a chamber of the heart through a vein or artery. Catheter 27 typically comprises a handle 28 for operation of the catheter by the physician. Suitable controls on handle 28 enable the physician to steer, locate and orient a distal end 29 of catheter 27 as desired.

System 20 comprises a positioning subsystem 30 that measures location and orientation coordinates of catheter 27. In the specification and in the claims, the term "location" refers to the spatial coordinates of an object such as catheter 27, the term "orientation" refers to angular coordinates of the object, and the term "position" refers to the full positional information of the object, comprising both location and orientation coordinates.

In one embodiment, positioning subsystem 30 comprises a magnetic position tracking system that determines the position of catheter 27. Positioning subsystem 30 generates magnetic fields in a predefined working volume in the vicinity of a patient, and senses these fields at catheter 27. Positioning subsystem 30 typically comprises a set of external radiators, such as field generating coils 31, which are located in fixed, known positions external to the patient. Coils 31 generate fields, typically magnetic fields, in the vicinity of heart 24.

A console 34 comprises a positioning processor 36 that calculates the location and orientation of catheter 27 based on the signals sent by a position sensor 32 in the catheter. Positioning processor 36 typically receives via cables 33 signals from sensor 32, and the processor amplifies, filters, digitizes, and otherwise processes the signals. Console 34 also comprises an image processor 43. As described below, processor 43 processes image data received by the console, and outputs the processed data as an image on a display 44. Console 34 comprises a pointing device 45, such as a trackball, a mouse, and/or a joystick, that allows the physician operating system 20 to control the system, typically via a graphic user interface (GUI) that the physician chooses to view. For clarity the GUI is not shown in FIG. 1. The GUI may be viewed on display 44, or on another display.

Some position tracking systems that may be used in embodiments of the present invention are described, for example, in U.S. Pat. No. 6,690,963, cited above, as well as in U.S. Pat. Nos. 6,618,612 and 6,332,089, and U.S. patent Application Publications 2004/0147920 A1 and 2004/0068178 A1, all of which are incorporated herein by reference. Although positioning subsystem 30 uses magnetic fields, embodiments of the present invention may be implemented using any other suitable positioning subsystem, such as systems based on electromagnetic field measurements, acoustic measurements and/or ultrasonic measurements.

Figure 2:
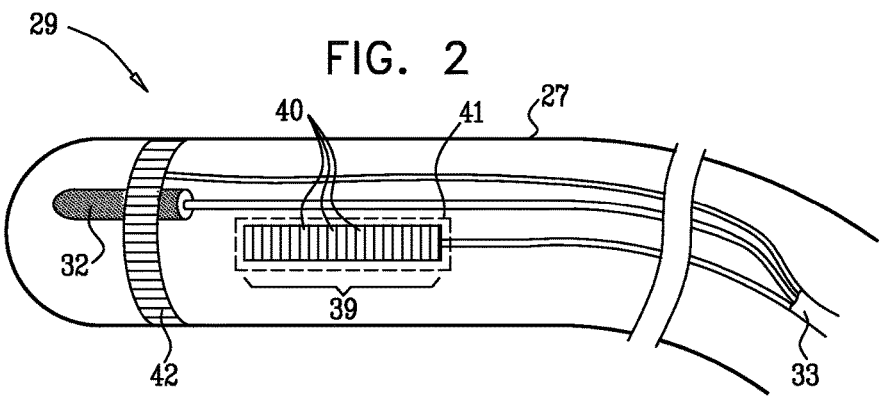
FIG. 2 is a pictorial illustration of the distal end of a catheter used in the system shown in FIG. 1, in accordance with an embodiment of the present invention.

FIG. 2 is a pictorial illustration of distal end 29 of catheter 27 used in the system shown in FIG. 1, in accordance with an embodiment of the present invention. The generated fields described above are sensed by position sensor 32 which transmits, in response to the sensed fields, position-related electrical signals over cables 33 to console 34. Alternatively, position sensor 32 may transmit signals to the console over a wireless link.

In an alternate embodiment, a radiator in the catheter, such as a coil, generates magnetic fields, which are received by sensors outside the patient's body. The external sensors generate the position-related electrical signals.

In some embodiments, catheter 27 comprises an ultrasonic imaging sensor 39. Ultrasonic imaging sensor 39 typically comprises an array of ultrasonic transducers 40. Although ultrasonic transducers 40 are shown arranged in a linear array configuration, other array configurations may be used, such as circular or convex configurations. In one embodiment, ultrasonic transducers 40 are piezo-electric transducers. Ultrasonic transducers 40 are positioned in or adjacent to a window 41, which defines an opening within the body or wall of catheter 27. Ultrasonic imaging sensor 39 produces an ultrasound image of heart 24 (FIG. 1), as described hereinbelow.

In some embodiments, distal end 29 of catheter 27 also comprises at least one electrode 42 for performing diagnostic functions, therapeutic functions, or both, such as electrophysiological mapping and radio frequency (RF) ablation. In one embodiment, electrode 42 may be used for sensing local electrical potentials, and the potentials may be used to generate a Carto map (described in more detail below). The electrical potentials measured by electrode 42 may be used in mapping the local electrical activity on the endocardial surface. When electrode 42 is brought into contact or proximity with a point on the inner surface of heart 24 (FIG. 1), the electrode measures the local electrical potential at that point. The measured potentials are converted into electrical signals and sent through catheter 27 to image processor 43 (FIG. 1). In other embodiments, the local electrical potentials are obtained from another catheter, generally similar to catheter 27, comprising suitable electrodes and a position sensor, all connected to console 34. (For clarity, the other catheter is not shown in FIG. 1.)

In alternative embodiments, electrode 42 may be used to measure parameters different from the electrical potentials described above, such as various tissue characteristics, temperature, and blood flow. Although electrode 42 is shown as being a single ring electrode, catheter 27 may comprise substantially any convenient number of electrodes, typically in a form known in the art. For example, catheter 27 may comprise two or more ring electrodes, a plurality or array of point electrodes, a tip electrode, or any combination of these types of electrodes for performing the diagnostic and therapeutic functions referred to above.

Position sensor 32 is typically located within distal end 29 of catheter 27, adjacent to electrode 42 and ultrasonic transducers 40. Typically, the location and orientation offsets between position sensor 32, electrode 42 and ultrasonic transducers 40 of ultrasonic imaging sensor 39 are constant. These offsets are typically used by positioning processor 36 (FIG. 1) to derive the positions of ultrasonic imaging sensor 39 and of electrode 42, given the measured position of position sensor 32. In another embodiment, catheter 27 comprises two or more position sensors 32, each having constant location and orientation offsets with respect to electrode 42 and ultrasonic transducers 40. In some embodiments, the offsets (or equivalent calibration parameters) are pre-calibrated and stored in positioning processor 36 (FIG. 1). Alternatively, the offsets may be stored in a memory device such as an electrically programmable read-only memory (EPROM), typically fitted into handle 28 of catheter 27.

Position sensor 32 typically comprises three non-concentric coils (not shown), such as are described in U.S. Pat. No. 6,690,963, cited above. Alternatively, any other suitable position sensor arrangement can be used, such as sensors comprising any number of concentric or non-concentric coils, Hall-effect sensors and/or magneto-resistive sensors.

In one embodiment, ultrasonic imaging sensor 39 comprises between sixteen and sixty-four ultrasonic transducers 40, typically between forty-eight and sixty-four ultrasonic transducers 40. Typically, ultrasonic transducers 40 generate ultrasound energy at a center frequency in a range of 5-10 MHz, with a typical penetration depth ranging from several millimeters to around 16 centimeters. The penetration depth depends upon the characteristics of ultrasonic imaging sensor 39, the characteristics of the surrounding tissue, and the operating frequency. In alternative embodiments, other suitable frequency ranges and penetration depths may be used.

Typically, ultrasonic imaging transducers 40 operate as a phased array, jointly transmitting an ultrasound beam from the array aperture through window 41. In one embodiment, the array transmits a short burst of ultrasound energy and then switches to a receive mode for receiving the ultrasound signals reflected from the surrounding tissue. Typically, ultrasonic imaging transducers 40 are driven individually in a controlled manner in order to steer the ultrasound beam in a desired direction. By appropriate timing of the transducers, the produced ultrasound beam may be given a concentrically curved wave front, so as to focus the beam at a given distance from the transducer array.

After receiving the reflected ultrasound, ultrasonic transducers 40 send electric signals based on the reflected ultrasound over cables 33 to image processor 43 in console 34. The processor generates ultrasound images from the signals, and uses the images and the positional information to produce a 3-dimensional ultrasound image of a target structure of the patient's heart.

Typically, both the ultrasound images and the position measurements are synchronized with the heart cycle, by gating signal and image captures relative to a body-surface electrocardiogram (ECG) signal or intra-cardiac electrocardiogram. In one embodiment, the ECG signal may be produced by electrode 42. Since features of the heart change their shape and position during the heart's periodic contraction and relaxation, the entire imaging process is typically performed at a particular timing with respect to this period.

In some embodiments, respective sets of images and position data are obtained at different times of the heart cycle. Each respective set of images and position data may be used to construct a 3-D image of the heart at a point in time, and the 3-D images may be combined to form a 4-D (time-varying) image.

Figure 3:
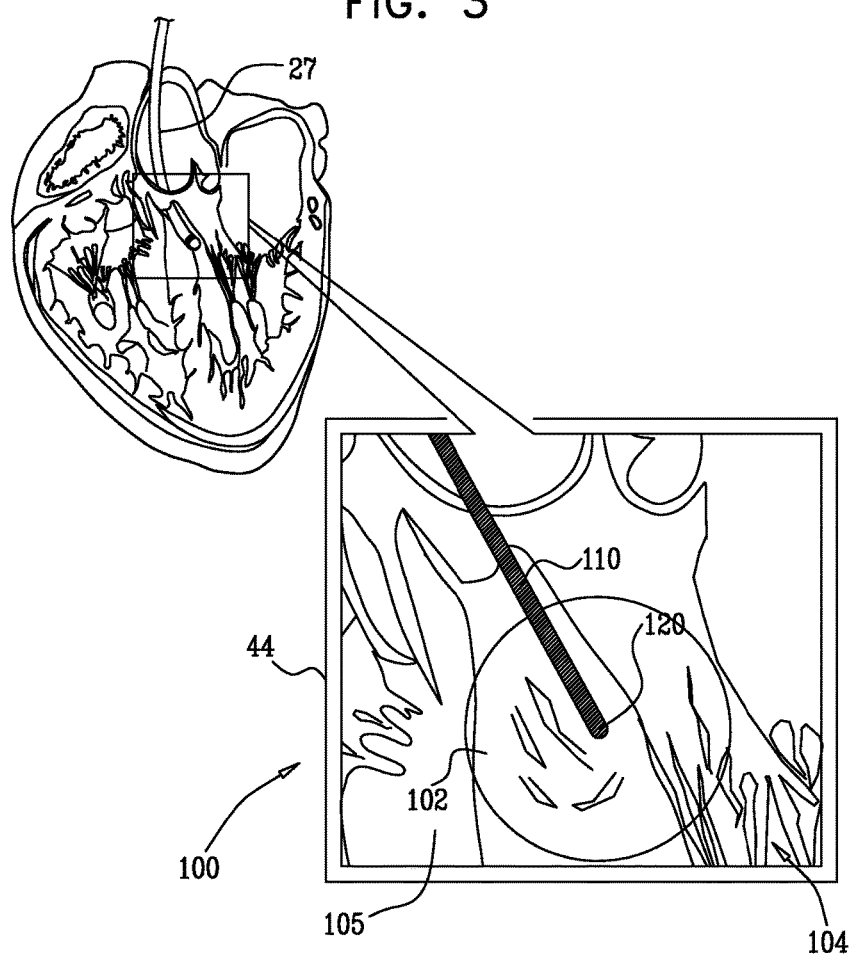
FIG. 3 is a schematic illustration of a flashlight view of a heart, in accordance with a disclosed embodiment of the present invention.

FIG. 3 is a schematic illustration of a flashlight view 100 of a heart, in accordance with a disclosed embodiment of the invention. Flashlight view 100 is generated on display 44. In flashlight view 100, a part 102 of a 3-D ultrasound image 104 of an anatomical structure is shown. Part 102 is also referred to herein as reconstruction region 102. Typically, an area of region 102 is in a range from approximately 10%-50% of the area of complete ultrasound image 104. Typically, the dimensions and boundaries of region 102, and consequently its area, may be adjusted by the operator of system 20, as described in more detail below. By way of example, in the following description the anatomical structure is assumed to be heart 24 (FIG. 1).

Within reconstruction region 102, image processor 43 generates a detailed portion of image 104. Processor 43 may also generate an icon 110, representing catheter 27, in registration with region 102. Outside reconstruction region 102, image processor 43 generates image 104 to have different parameters from those of region 102. The differences between the two parts of image 104 typically comprise differences in color, hue, intensity, transparency/opacity, resolution, or other image parameters, or a combination of these parameters. Typically the differences are chosen to enhance the visibility of elements within reconstruction region 102, compared to the visibility of elements outside the region.

By way of example, reconstruction region 102 is assumed to correspond to an approximately planar section of heart 24 that is intersected by a sphere centered on a tip 120 of icon 110. In this case, the reconstruction region is in direct registration with tip 120. The size of reconstruction region 102 may be set by the operator, typically by the operator changing a size parameter via a graphic user interface (GUI) presented to the operator on display 44 (FIG. 1). In some embodiments of the invention, the center of the reconstruction region may be a point other than the tip 120, so that the reconstruction region is not in direct registration with tip 120. For example, the center may be in a fixed direction relative to the tip, defined by the operator. Additionally or alternatively, the center may be adjusted by the operator operating pointing device 45.

The operator of system 20 may define the dimensions of region 102 according to other criteria. For example, one criterion may comprise a direction of the ultrasound beam issuing from distal end 29, and the operator may define dimensions of a slice, in the general direction of the beam, that are to be used to delineate region 102. Alternatively or additionally, the operator may use a pointing device, such as device 45, in conjunction with display 44, to delineate the dimensions of region 102. In some embodiments, the operator may relocate the region defined by a pointing device to a desired location on display 44.

In some embodiments, only elements of image 104 within region 102 are shown on display 44, and elements outside the region are displayed with no image information. For example, processor 43 may set the intensity of the image parameters outside region 102 to be effectively zero, or to comprise a single color.

Figure 4A:
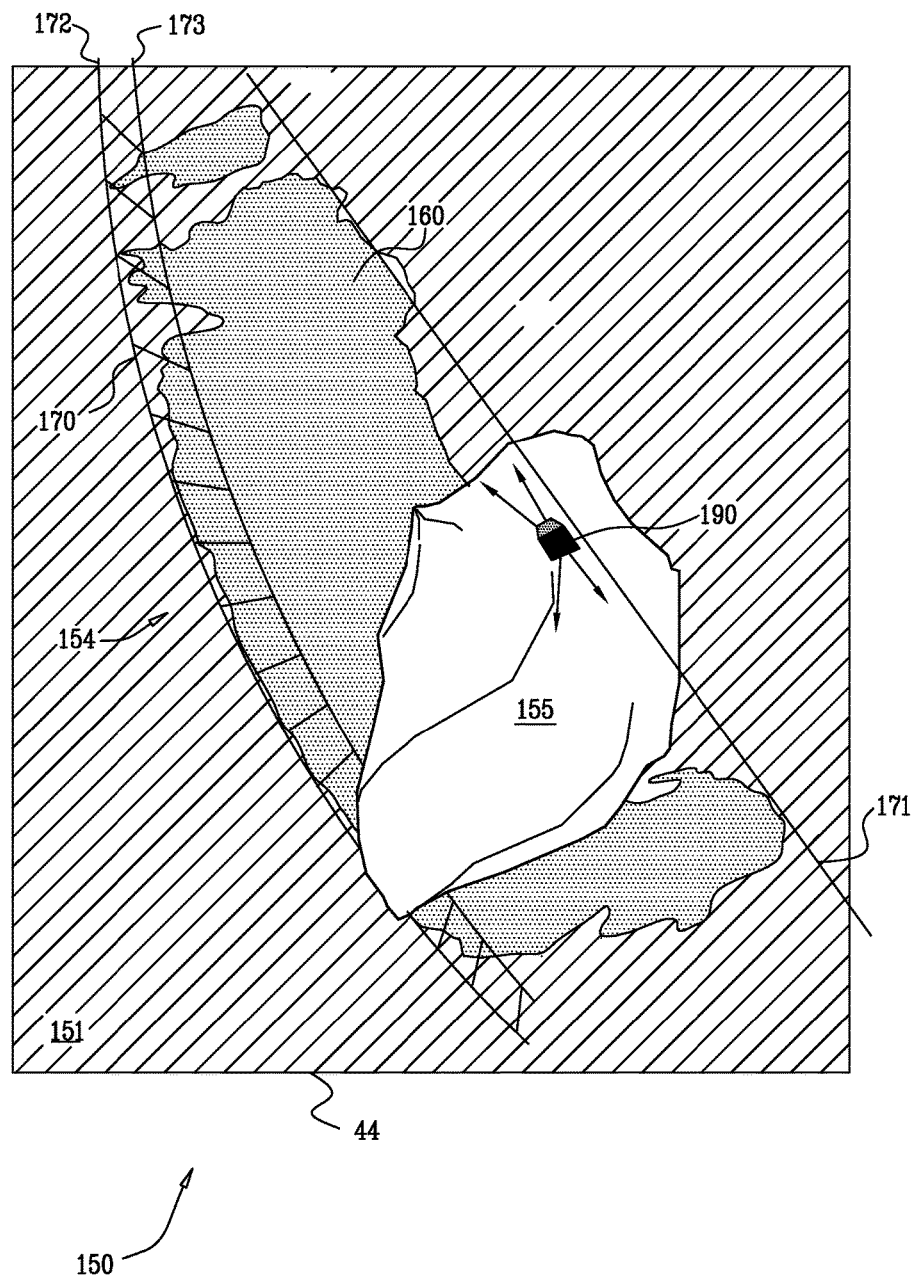
FIG. 4A is a schematic illustration of a flashlight view of a heart, in accordance with an alternate embodiment of the present invention.

Reference is now made to FIG. 4A, which is a schematic illustration of a flashlight view 150 of a heart, in accordance with an alternative disclosed embodiment of the invention. As for view 100, flashlight view 150 is shown on display 44. Flashlight view 150 differs from flashlight view 100 (FIG. 3) in that view 100 is generated substantially only from an ultrasound image (image 104), whereas in view 150 an ultrasound image is appended to another type of image.

In FIG. 4A, a Carto map 155 is shown. Carto map 155 is a 3-D color coded, or a 3-D gray scale coded, electro-anatomical map of a heart which may be obtained, for example, using the Carto-Biosense® Navigation System, available from Biosense Webster Inc., 3333 Diamond Canyon Road, Diamond Bar, Calif. 91765. On display 44, Carto map 155 is shown in different colors and shadings, typically on a black background. In FIG. 4A, the Carto map is shown as a mainly white region. A region 151 in FIG. 4A, which is shown as black on display 44, is represented by parallel diagonal hatching in the figure.

Flashlight view 150 is formed by appending only a reconstruction region 154, formed from a larger ultrasound image, to map 155. For clarity, the larger ultrasound image is not shown in FIG. 4A, but typically the larger ultrasound image would cover substantial sections of region 151. In FIG. 4A, reconstruction region 154 is shown as a dotted region, and defines a smaller ultrasound image 160 that is produced from the larger ultrasound image. Reconstruction region 154 is generally similar to a spherical lune, and may be thought of as being generally similar to a section of orange peel, having a finite thickness. The operator is assumed, by way of example, to delineate region 154, including its boundaries and thickness, using an icon 190 and the arrows associated with the icon together with pointing device 45. For example, the ends of the arrows may be implemented as "handles" that allow the user to adjust the reconstruction region dimensions. However, any other convenient method for delineating the region may be used. Icon 190 represents distal end 29 of catheter 27. Region 154 is bounded by a first plane, shown in FIG. 4A as a region 170 having non-parallel hatch lines, and a second plane, shown as a line 171. A separation between the two curved lines 172, 173 defining region 170 illustrates the thickness of region 154.

In flashlight view 150 reconstruction region 154 is appended to map 155, so that the map appears to be superimposed over the region. Outside reconstruction region 154 and map 155, the larger ultrasound image is not displayed (it has an intensity of zero).

The description above has assumed that a Carto map is used in flashlight view 150. Other maps, such as an MRI map or a CT map, may be used in place of the Carto map in the flashlight view, and all such maps are assumed to be included in the scope of the present invention.

Figure 4B:
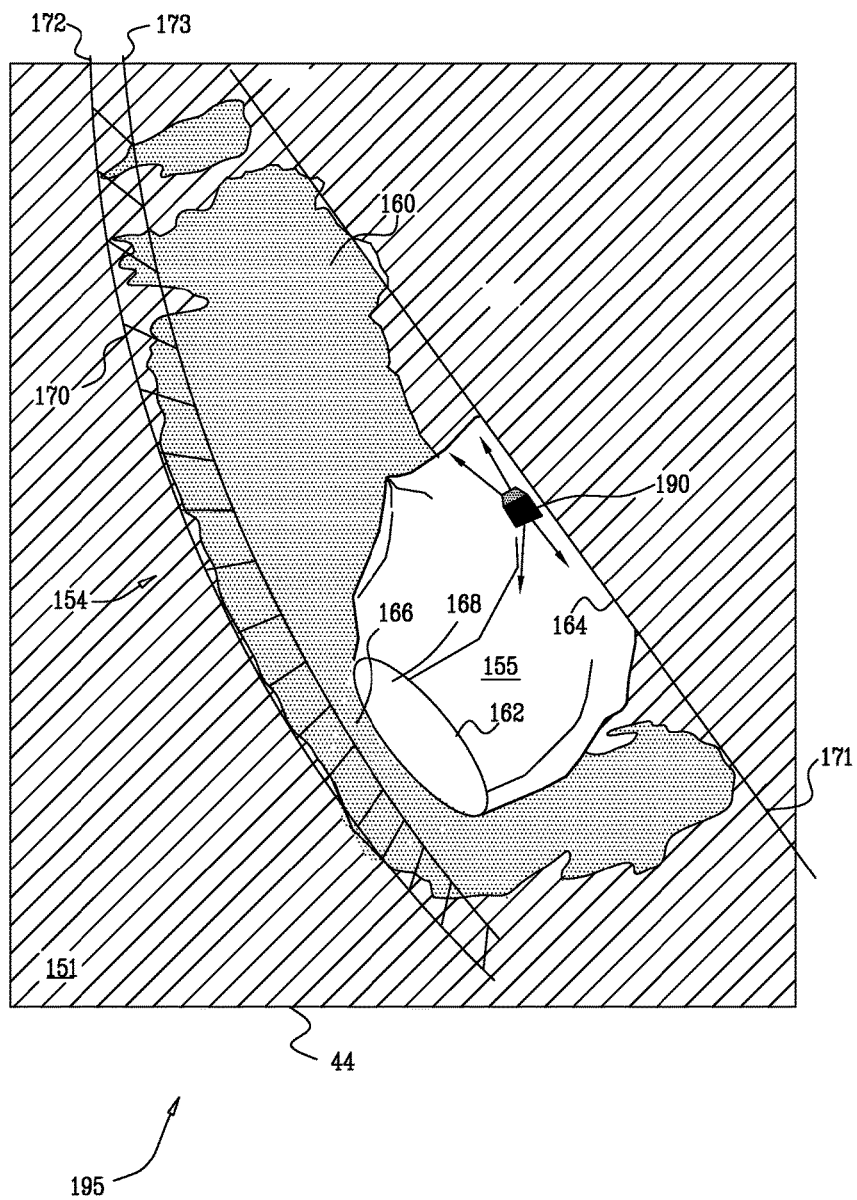
FIG. 4B is a schematic illustration of a flashlight view of a heart, in accordance with a further alternate embodiment of the present invention.

FIG. 4B is a schematic illustration of a flashlight view 195 of a heart, in accordance with a further alternative disclosed embodiment of the invention. Apart from the differences described below, flashlight view 195 is generally similar flashlight view 150, and elements indicated by the same reference numerals in both views are generally similar in construction and in operation. In flashlight view 195, the operator includes map 155 in the definition of the reconstruction region, so that the map is redefined by being truncated. Planes defining truncations of the map are shown schematically in FIG. 4B by an ellipse 162 and a section 164 of line 171. In flashlight view 195 a portion 166 of region 154 that is obscured in view 150 is thus visible to the operator. In a yet further embodiment, the operator may make at least partially visible a portion 168 of region 154 that is within ellipse 162.

Reference is now made to FIG. 5, which is a flowchart 201 illustrating a method of displaying a flashlight view, in accordance with a disclosed embodiment of the invention. The method is explained with reference to flashlight views 100, 150, and 195 of FIGS. 3, 4A and 4B respectively.

In an initial step 205, a first spatial representation of heart 24 is acquired. In the example of FIG. 3, the first spatial representation comprises 3-D ultrasound image 104; in the examples of FIGS. 4A and 4B, the first spatial representation comprises map 155. In alternative embodiments, the first spatial representation may comprise an electro-anatomical map, a CT (Computed Tomographic) image, an MR (Magnetic Resonance) image, or any other image of heart 24, or a combination of such images.

At a decision step 207, the operator decides whether there are any other types of spatial representation to be displayed. The result of decision step 207 typically depends on the spatial representations available to the operator, and/or options selected by the operator. In the example of FIG. 3, the result of decision step 207 is negative. In the examples of FIGS. 4A and 4B, the result of decision step 207 is affirmative at a first pass and negative at a second pass. In some embodiments of the present invention, more than one extra spatial representation is selected by the operator, for example the operator may select a CT map and an MR map, so that there is more than one pass through step 207.

If the determination at decision step 207 is affirmative, then control proceeds to a step 210, wherein an additional spatial representation is acquired. The additional spatial representation may comprise any of the types described herein with reference to initial step 205. In the examples of FIGS. 4A and 4B, the additional spatial representation comprises the larger ultrasound map referred to above with reference to FIGS. 4A and 4B. The additional spatial representations are typically pre-acquired, possibly in segments that are then reconstructed. However, the additional spatial representations may be acquired during implementation of flowchart 201.

In a step 215, image processor 43 registers the two representations. Thus, the larger ultrasound image referred to above with reference to FIGS. 4A and 4B is placed in registration with map 155 to create a composite or combined image. Suitable registration techniques are disclosed in U.S. Pat. No. 6,650,927, which is assigned to the assignee of the present invention, and which is incorporated herein by reference. For example, landmarks and/or other fiducial marks common to both the larger ultrasound image and Carto map 155 are identified, typically automatically, but alternatively or additionally with assistance from the operator. The scale of the larger ultrasound image is adjusted and the image is repositioned and rotated until the common features are aligned. Control returns to decision step 207.

If the determination at decision step 207 is negative, then control proceeds to a step 218. In step 218, the user specifies parameters for display of the composite image, typically using a GUI. The parameters define visual modes for display of the spatial representations, and comprise first display parameters for display inside the reconstruction region (described above) and second display parameters for display outside the reconstruction region. The parameters may include, inter alia, resolution, intensity, color, and transparency (i.e. transparent, partially transparent, or opaque). The parameters may also include whether an icon of a catheter or other instrument is to be displayed. In some embodiments of the invention, the parameters may have been pre-selected, in which case step 218 may be considered as being performed before step 205.

In a step 220, positioning processor 36 determines the location and orientation of distal end 29 of catheter 27. Methods for determining the location and orientation of distal end 29 of catheter 27 are described hereinabove in reference to FIG. 1.

In a step 225, performed if an icon of the catheter is to be displayed, image processor 43 places icon 110 (FIG. 3) or icon 190 (FIGS. 4A and 4B), representing distal end 29 of catheter 27, in registration with the image available after step 207 has returned a negative answer. The image is a composite image if step 215 has been performed. If step 215 has not been performed, the image consists of the first spatial representation.

In a step 230, the operator specifies the shape and size of the reconstruction region relative to end 29 determined in step 220, typically by the operator changing size parameters via a graphical user interface (GUI) presented to the user on display 44 (FIG. 1), and/or by the operator adjusting the dimensions of the region as described above with reference to FIG. 4A. In some embodiments of the invention, the user may specify a dimensions of the reconstruction region by adjusting pointing device 45 or by specifying additional parameters, e.g. a distance from distal end 29 of catheter 27 in the direction of an ultrasound beam. In other embodiments of the invention, the center of the reconstruction region may be the distal end of the catheter.

In a step 235, image processor 43 determines the extents of the reconstruction region from the values input in step 230, and applies the image parameters of step 218 to the region and to the remainder of the image to be presented on display 44.

Thus, in the case of flashlight view 100 (FIG. 3), processor 43 determines the extents of reconstruction region 102, and applies the image parameters of step 218 within the region and outside the region. Parameters for icon 110 with its tip 120 centered on reconstruction region 102 may also be calculated. Typically, the image parameters within region 102 provide more detail, and/or better visibility to the operator, than the image parameters outside the region.

In the case of flashlight view 150 (FIG. 4A), the processor 43 determines the extents of reconstruction region 154, and applies the image parameters of step 218 within the region and outside the region. The dimensions of region 154 are only applied to the larger ultrasound image (described above with reference to FIG. 4A). In flashlight view 150, the image parameters append map 155 so that it appears to obscure part of the underlying ultrasound image, and so that the complete map 155 is displayed.

Flashlight view 195 (FIG. 4B) is generally similar to view 150, except that the dimensions of region 154 are also applied to map 155, so that the map is truncated to conform with the operator defined dimensions of region 154.

In a final step 240 of flowchart 201, image processor 43 presents a 2-D projection of the flashlight view determined in step 235 on display 44.

Typically, image processor 43 (FIG. 1) iterates flowchart 201 so as to provide the flashlight view to the operator substantially continuously, and in real-time.

It should be understood that the steps of flowchart 201 need not necessarily be performed in the order shown. For example, step 210 may be performed before, or concurrently with, step 205. Other variations in the order will be apparent to those skilled in the art.

It will also be understood that flashlight views 100, 150, and 195 are provided herein by way of example, and that other types of flashlight view may be presented to the operator on display 44.

For example, referring to flashlight view 100, instead of display 44 showing region 102 and an area outside the region, the operator may choose to show only region 102, and to have display 44 provide no image information outside the region, for example by having the area outside the region as one color such as black.

Referring to flashlight view 150, the operator may choose to show only ultrasound image 160 with no image information outside the region, or to append image 160 to map 155 so that the image appears to be superimposed on the map. In the latter case the image appears to obscure the map. Alternatively, the operator may choose the parameters in step 218 so that there is no obscuration, by making the image or the map partially transparent where they overlap.

Referring to flashlight view 195, the operator may choose to show only truncated map 155, and not show ultrasound image 160. Alternatively, at least part of the truncated map may be made partially transparent so that underlying ultrasound image 160 defined by region 154 is visible.

In an alternative embodiment, techniques described herein may be applied to other anatomical structures, for example organs apart from the heart, such as the stomach.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for imaging an anatomical structure and displaying a flashlight view of the anatomical structure on a display, comprising:

acquiring an initial spatial representation of the anatomical structure, wherein the initial spatial representation of the anatomical structure is a 3-D image of the anatomical structure, and displaying at least part of the 3-D image of the anatomical structure on a display;

positioning an instrument in proximity to the anatomical structure by inserting the instrument through a vein or artery;

determining a location of the instrument by measuring spatial and orientation coordinates of a tip of the instrument;

generating:

(i) a reconstruction region image, wherein the reconstruction region image corresponds to a portion of the 3-D image of the anatomical structure, wherein the reconstruction region image is a 2-D image representing a planar section of the anatomical structure, wherein the 2-D reconstruction region image is overlaid on the corresponding portion of the 3-D image of the anatomical structure on the display, and wherein the 3-D image of the anatomical structure and the reconstruction region image have the same scale and are different portions of a single composite image of at least part of said anatomical structure; and (ii) an icon of the tip of the instrument based on the spatial and orientation coordinates of the tip of the instrument, wherein the icon is displayed on the display within the reconstruction image and in a position corresponding to the current location of the tip of the instrument with respect to the anatomical structure;

setting a size parameter of the reconstruction region via a graphic user interface (GUI) on the display, wherein the size of the reconstruction region image of the anatomical structure is from 10%-50% of the area of the 3-D image of the anatomical structure on the display;

wherein one or more different display parameters are used to display the 3-D image of the anatomical structure and the reconstruction region image, and wherein the different display parameters are chosen from intensity, color, resolution, and transparency in order to visibly distinguish elements within the reconstruction region image from elements of the 3-D image of the anatomical structure which are outside of the reconstruction region image on the display;

wherein the position of the reconstruction region on the display and with respect to the 3-D image of the anatomical structure is defined in relation to the position of the tip of the instrument, and wherein the reconstruction region is moved on the display and with respect to the 3-D image of the anatomical structure to follow movement of the tip of the instrument;

wherein the step of setting the size parameter of the reconstruction region comprises:

displaying a plurality of handles associated with the icon on the GUI, wherein each of the handles is a movable element on the GUI;

an operator moving at least one of the handles on the GUI and thereby adjusting at least one of a shape and a size of the reconstruction region and thereby changing one or more boundaries of the reconstruction region; and after said adjustment, displaying the reconstruction region on the display according to said operator adjustment, and moving the reconstructions region on the display to follow movement of the tip of the instrument while the instrument is moved within the anatomical structure wherein the reconstruction region is delineated, including the boundaries of the reconstruction region, using the icon and arrows associated with the icon, together with a pointing device, wherein the ends of the arrows are the handles.

2. The method according to claim 1, wherein the instrument comprises a catheter configured to generate an ultrasound beam, and wherein the reconstruction region is shaped and oriented in relation to a direction of the ultrasound beam.

3. The method according to claim 1,
wherein the reconstructions region is shaped as a spherical lune.

4. The method according to claim 1,
wherein the anatomical structure is a heart;
the method further comprising capturing an electrocardiogram (ECG) signal, and
based on the ECG signal, capturing successive images at a same time point with respect to periodic contraction of the heart.

5. The method of claim 1, wherein the initial spatial representation comprises at least one of a Carto map, a Computed Tomographic (CT) image, and a magnetic resonance (MR) image.

6. The method of claim 1,
wherein the initial spatial representation providing the 3-D image of the anatomical structure comprises an ultrasound image, and
wherein the 2-D reconstruction region image depicts a circular section of said ultrasound image;
wherein the circular section of the ultrasound image is centered on the icon of the tip of the instrument.

7. The method of claim 1,
wherein the instrument comprises a catheter having a catheter tip;
wherein the anatomical structure is a heart;
wherein an operator inputs at least one of a shape and a size for the reconstruction region, and the reconstruction region is displayed on the display according to said at least one of shape and size;
wherein said positioning of the instrument comprises moving the catheter in the heart;
wherein the reconstruction region image is registered with the catheter tip, and moves on the display with the catheter tip.

8. A computer software product for imaging an anatomical structure and displaying a flashlight view of the anatomical structure on a display, comprising a tangible computer-readable medium in which computer instructions are stored, which instructions, when read by a computer operatively linked to an instrument positioned in proximity to an anatomical structure and to a display, cause the computer to perform the method according to claim 1.

9. Apparatus for imaging an anatomical structure and displaying a flashlight view of the anatomical structure, comprising:
a display having a graphic user interface (GUI);
an instrument which is configured to be positioned in proximity to the anatomical structure, the instrument being inserted through a vein or artery; and a processor, which is configured to be coupled to the instrument, and which is arranged to acquire an initial spatial representation of the anatomical structure as a 3-D image of the anatomical structure, to determine a location of the instrument by measuring spatial and orientation coordinates of a tip of the instrument, to generate, in response to the spatial and orientation coordinates of the tip of the instrument:
(i) a reconstruction region image, wherein the reconstruction region image corresponds to a portion of the 3-D image of the anatomical structure, wherein the reconstruction region is a 2-D image representing a planar section of the anatomical structure, wherein the reconstruction region image is overlaid on the corresponding portion of the 3-D image of the anatomical structure on the display, and wherein the 3-D image of the anatomical structure and the reconstruction region image have the same scale and are different portions of a single composite image of at least part of said anatomical structure; and
(ii) an icon of the tip of the instrument based on the spatial and orientation coordinates of the tip of the instrument, wherein the icon is displayed on the display within the reconstruction image and in a position corresponding to the current location of the tip of the instrument with respect to the anatomical structure;
wherein the reconstruction region image is 10%-50% of the area of the 3-D image of the anatomical structure on the display,
wherein one or more image display parameters being used in the reconstruction region image are different from the display parameters being used outside of the reconstruction region image in the 3-D image of the anatomical structure, wherein the parameters are chosen from intensity, color, resolution, and transparency in order to enhance the visibility of elements within the reconstruction region image compared to the elements of the 3-D image of the anatomical structure outside of the reconstruction region image on the display, and
wherein the position of the reconstruction region on the display and with respect to the 3-D image of the anatomical structure is defined in relation to the position of the tip of the instrument, and wherein the reconstruction region is moved on the display and with respect to the 3-D image of the anatomical structure to follow movement of the tip of the instrument
wherein the reconstruction region is delineated, including the boundaries of the reconstruction region, using the icon and arrows associated with the icon, together with a pointing device, wherein the ends of the arrows are movable elements on the display.

10. The apparatus according to claim 9, wherein the instrument comprises a catheter configured to generate an ultrasound beam, and
wherein the reconstruction region is defined and positioned in relation to a direction of the ultrasound beam.

11. The apparatus according to claim 9,
wherein the instrument is a catheter comprising a catheter tip and a position sensor; and
wherein the position of the reconstruction region on the display is defined in relation to the catheter tip and is moved to follow movement of the catheter tip.

12. The apparatus of claim 9,
wherein the initial spatial representation providing the 3-D image of the anatomical structure comprises an ultrasound image, and
wherein the reconstruction region image depicts a 2-D section of said ultrasound image.

13. A method for imaging a heart and displaying a flashlight view of the heart on a display, comprising:
acquiring an initial spatial representation of at least part of the heart using ultrasound, wherein the initial spatial representation comprises a 3-D ultrasound image of at least part of the heart;
positioning a catheter in proximity to the heart by inserting the catheter into a patient, wherein the catheter comprises both a position sensor, and an electrode capable of sensing local electrical potentials, at a tip;
determining a series of locations of the catheter by measuring spatial and orientation coordinates of the tip of the catheter;

moving the catheter in the heart, and sensing local electrical potentials at a plurality of surface positions in the heart using the electrode;

(i) displaying a reconstruction region on the display, wherein the reconstruction region is a subsection of the initial spatial representation of the heart comprising a 3-D ultrasound image, wherein the reconstruction region is overlaid on the corresponding portion of the initial spatial representation on the display, and wherein the initial spatial representation and the reconstruction region have the same scale and are different portions of a single composite image of at least part of the heart; and (ii) displaying an icon representing the tip of the instrument, wherein the icon is displayed on the display within the reconstruction region and in a position corresponding to the current location of the catheter tip with respect to the heart;

(iii) displaying an Electroanatomical Map of the heart using said local electrical potentials sensed by the electrode and corresponding position data from the position sensor, the Electroanatomical Map being a three-dimensional map depicting different electrical potentials on respective surface areas of the heart using at least one of different colors and differential shading, wherein the Electroanatomical Map is overlaid on and partially obscures the reconstruction region on the display;

wherein one or more different display parameters are used to display the reconstruction region and areas of the initial spatial representation outside of the reconstruction region, so that they are visually distinguishable on the display; and wherein the position of the reconstruction region on the display and with respect to the initial spatial representation is defined in relation to the position of the tip of the catheter, and wherein the reconstruction region is moved on the display and with respect to the initial spatial representation of the heart to follow movement of the tip of the catheter wherein the reconstruction region is delineated, including the boundaries of the reconstruction region, using the icon and arrows associated with the icon, together with a pointing device, wherein the ends of the arrows are movable elements on the display.

14. The method of claim 13,
wherein the size of the reconstruction region image is from 10%-50% of the area of the initial spatial representation on the display.

15. The method of claim 13:
wherein an operator selects first display parameters for the reconstruction region, and second display parameters for portions of the initial spatial representation outside of the reconstruction region;
wherein the first display parameters and the second display parameters differ from each other as to at least one of resolution, intensity, color, and opacity;
the method comprising displaying the reconstruction region according to the first display parameters, and displaying the initial spatial representation outside the reconstruction region using the second display parameters.

16. The method of claim 13:
wherein all of the Electroanatomical Map is displayed on the display.

17. The method of claim 13:
wherein only areas of the Electroanatomical Map within the reconstruction region are shown on the display.

18. The method of claim 13: wherein areas of the initial spatial representation outside of the reconstruction region have a display intensity of zero, and are therefore not visible on the display.

19. The method of claim 13, wherein the reconstruction region is displayed as a 2-D image.

* * * * *